United States Patent
Burghardt et al.

(10) Patent No.: US 9,023,073 B2
(45) Date of Patent: May 5, 2015

(54) MULTI-TROCAR SYSTEM

(75) Inventors: Jens Burghardt, Woltersdorf (DE);
Juergen Bogenschuetz, Altheim (DE);
Daniel Weinmann, Seitingen-Oberflacht (DE)

(73) Assignee: Karl Storz GmbH & Co. KG (DE)

( * ) Notice: Subject to any disclaimer, the term of this patent is extended or adjusted under 35 U.S.C. 154(b) by 161 days.

(21) Appl. No.: 13/414,459

(22) Filed: Mar. 7, 2012

(65) Prior Publication Data

US 2012/0232572 A1 Sep. 13, 2012

(30) Foreign Application Priority Data

Mar. 7, 2011 (DE) .......................... 10 2011 013 889

(51) Int. Cl.
*A61B 17/34* (2006.01)
*A61B 17/00* (2006.01)

(52) U.S. Cl.
CPC ... *A61B 17/3421* (2013.01); *A61B 2017/00477* (2013.01); *A61B 2017/3447* (2013.01)

(58) Field of Classification Search
CPC .............. A61B 17/34; A61B 17/3415; A61B 17/3403; A61B 17/3423; A61B 17/3494; A61B 17/3496; A61B 2017/3433; A61B 2017/3445
USPC ................... 606/185, 184, 186, 108, 75, 219; 604/164.01, 164.09, 164.11, 264, 523, 604/533, 534; 600/566–567
See application file for complete search history.

(56) References Cited

U.S. PATENT DOCUMENTS

| | | | |
|---|---|---|---|
| 3,299,883 A | | 1/1967 | Rubens |
| 4,146,022 A | * | 3/1979 | Johnson et al. ................. 606/74 |
| 5,290,276 A | | 3/1994 | Sewell, Jr. |
| 5,569,205 A | | 10/1996 | Hart et al. |
| 5,593,423 A | * | 1/1997 | Person et al. ................. 606/219 |
| 5,797,835 A | * | 8/1998 | Green ........................... 600/106 |
| 6,171,339 B1 | * | 1/2001 | Houfburg et al. .......... 623/17.16 |
| 6,371,968 B1 | | 4/2002 | Kogasaka et al. |
| 6,969,392 B2 | * | 11/2005 | Gitis et al. ....................... 606/87 |
| 7,427,287 B2 | * | 9/2008 | Turovskiy et al. ............ 606/185 |
| 2007/0282266 A1 | * | 12/2007 | Davidson ................. 604/164.01 |
| 2008/0319436 A1 | * | 12/2008 | Daniel et al. .................... 606/33 |
| 2010/0249808 A1 | * | 9/2010 | Harada et al. ................. 606/144 |

FOREIGN PATENT DOCUMENTS

| | | |
|---|---|---|
| DE | 69528176 T2 | 1/2003 |
| EP | 0241159 A2 | 10/1987 |
| EP | 2163217 A2 | 3/2010 |
| WO | 2007140449 A2 | 12/2007 |
| WO | 2009070896 A1 | 6/2009 |
| WO | 2012014656 A1 | 2/2012 |

OTHER PUBLICATIONS

Catalogue Laparoskopie, 3rd Edition Feb. 1999, p. TROC 20 B.

* cited by examiner

*Primary Examiner* — Julian W Woo
*Assistant Examiner* — Shaun L David
(74) *Attorney, Agent, or Firm* — St. Onge Steward Johnston & Reens LLC

(57) ABSTRACT

A trocar mandrel comprises a head, a first mandrel having an elongated shaft, a proximal end of said first mandrel being mounted at said head. At least a second trocar mandrel having an elongated shaft is mounted at said head. Said mandrels are mounted at a distance one to another and project from a distal face of said head.

7 Claims, 6 Drawing Sheets

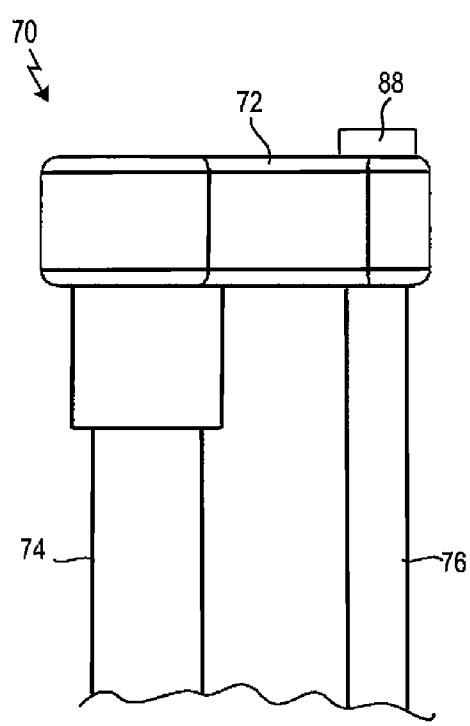
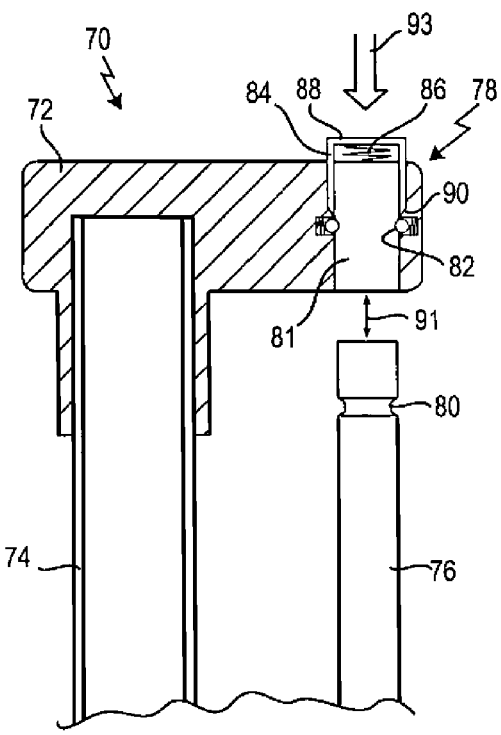
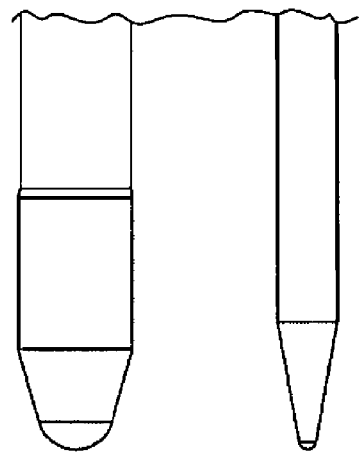
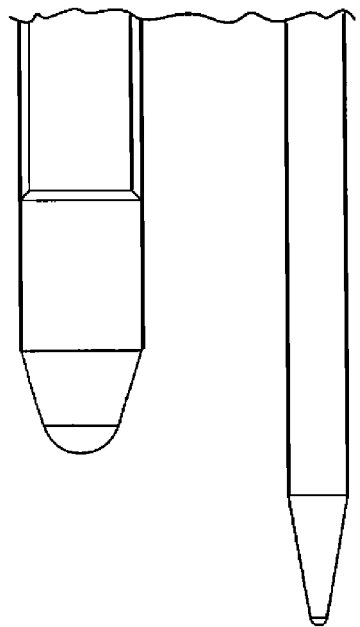
Fig. 7  Fig. 8

MULTI-TROCAR SYSTEM

BACKGROUND OF THE INVENTION

The invention relates to a trocar mandrel.

Trocar mandrels of this kind are in widespread use in minimally invasive surgery and are known, for example, from the catalogue Laparoskopie [Laparoscopy], 3rd edition 2/99, page TROC 20 B, from Karl Storz GmbH & Co KG, Tuttlingen, Germany.

A trocar is composed of a trocar sleeve and of a trocar mandrel that is to be pushed into the latter. The trocar mandrel is dimensioned such that it fills the interior of the trocar sleeve, and such that its tip extends distally beyond the trocar sleeve. It is known to give the tip of the trocar mandrel different geometries, for example a blunt tip, a conical tip or a three-edged tip.

The assembled device made up of trocar sleeve and trocar mandrel, i.e. the trocar, is used to create an access to an internal cavity of the body in minimally invasive surgery.

A widespread area of application is laparoscopy.

In laparoscopy, an incision measuring approximately 1 to 2 cm in length is made in the skin of the abdominal wall. The trocar is applied to this incision via the tip of the trocar mandrel protruding from the trocar sleeve. The assembled device is then pushed through the abdominal wall until the distal end of the device protrudes into the abdominal space. The trocar mandrel is then withdrawn and discarded.

The hollow trocar sleeve now engages in the body, for example in the abdominal wall, and a minimally invasive intervention can then be performed through the trocar sleeve.

The external diameter of a trocar sleeve is up to about 25 mm, such that the space for passing instruments through the trocar sleeve is relatively small.

In minimally invasive interventions, it has become customary, particularly in laparoscopy, to apply several such trocar sleeves. In this way, different medical instruments can then be inserted through the several trocar sleeves, for example instruments having purely a monitoring purpose, e.g. endoscopes, and medical working instruments, such as forceps, scissors, punches and the like, and also instruments for supplying media, for example gaseous media for inflating the abdominal space, or irrigation liquids for flushing blood, in particular, from the operating site.

In a number of operating techniques, it has been found to be expedient for two adjacent trocars to be inserted at a very defined distance from each other into the body. This is especially the case when a monitoring instrument pushed through a first trocar sleeve is intended to specifically monitor the working area of another instrument that is pushed through a second trocar sleeve.

The operator needs to have considerable experience to apply two or more trocars at an exactly defined distance from each other.

It is, therefore, an object of the present invention to provide a trocar system allowing to set several trocars at defined distances.

SUMMARY OF THE INVENTION

According to the invention, the object is achieved by a trocar mandrel, comprising a head, a first mandrel having an elongated shaft, a proximal end of said first mandrel being mounted at said head, said shaft having a tip at its distal end, at least a second trocar mandrel having an elongated shaft, a proximal end of said second mandrel being mounted at said head part, said first and second mandrels are mounted at a distance one to another and project from a distal face of said head.

In the simplest case, a second elongated shaft-like mandrel is provided, thereby resulting as it were in a twin trocar mandrel, in which the two shaft-like mandrels are arranged on one and the same head and extend away from the latter. It is possible in principle for more than two mandrels to be arranged on one head.

It is thus possible to arrange these mandrels in a very defined orientation, in most cases parallel to each other and at a very defined distance from each other. It is possible to have the mandrels slightly tilted, as long as the mandrels can be pushed into a body with one movement.

A trocar sleeve can now be pushed over each of the mandrels, and the resulting trocar is then an assembled device comprising a single head from which there extend several mandrels, onto each of which a trocar sleeve is pushed.

In laparoscopy, for example, this compact assembled device can be placed on the corresponding incisions in the abdominal wall and, in a single step, pushed through the abdominal wall. A further advantage is that the necessarily relatively large head of the trocar mandrel can function as a "pusher", via which the operating surgeon's hand applies to the trocar the force that is needed to drive the latter through the abdominal wall.

After application, the trocar mandrel can then be withdrawn in one step from the correspondingly applied trocar sleeves, whether there are two, three or more of these.

The trocar sleeves now remaining in the body are precisely oriented and, in particular, are at the desired defined distance from each other.

This considerably facilitates the minimally invasive intervention that is performed through several trocar sleeves. A further advantage is also that such a trocar, having a trocar mandrel according to the invention with several mandrels, constitutes a relatively compact and slim structure that can be inserted initially into already existing body cavities and only then is driven onwards through the tissue into body cavities lying further to the inside.

This is very advantageous, for example, in operating techniques practiced in the lower region of the female abdomen, where the trocar with the several trocar sleeves can initially be pushed through the vagina and, only in the area of the uterus or, for example, of the recto-uterine pouch, can be driven through the tissue into the inner body cavity.

This can be done much more easily and in a single step compared to a situation where several individual trocars are guided in succession through the vagina as far as these internal tissue regions. In the final analysis, therefore, the trocars can also be applied in a manner that is much less traumatic for a female patient.

In another embodiment of the invention, the mandrels have different diameters.

This measure has the advantage that different trocar sleeves that are suitable for one type of operation and that have different diameters can be used simultaneously. For example, a trocar sleeve with a relatively large diameter can be applied through which relatively bulky working instruments are pushed, and at the same time a relatively slim trocar sleeve of smaller diameter can be applied through which only a monitoring instrument, e.g. an endoscope, is pushed.

This permits a high degree of flexibility and a particularly atraumatic application of trocar sleeves of different diameter.

In another embodiment of the invention, the head has a proximal cover surface serving as a grip.

This measure has the advantage that this proximal cover surface can serve as an engagement surface, for example for a hand of the operating surgeon, in order to exert the force needed to push the trocar through the tissue.

In another embodiment of the invention, the head, seen towards the proximal cover surface, is designed as a rounded body.

This measure has the advantage that the head is designed particularly ergonomically, i.e. without corners and edges, such that it can be gripped particularly ergonomically by the operating surgeon.

In another embodiment of the invention, a circumferential profile of the cover surface corresponds to a contour line enveloping the mandrels.

This measure has the advantage that, here too, a particularly ergonomic and rounded body is created. At the same time, in the case of trocar mandrels with mandrels of different diameter, this results in a contour line that is visible in each case from the outside and that shows the operating surgeon on which side the mandrel of greater diameter is arranged and on which side the mandrel of smaller diameter is arranged.

Returning to the previously mentioned example of transvaginal insertion, a considerable portion of the elongate body is already inserted into the vagina shortly before the trocar is pushed into the tissue, and this portion cannot therefore be seen, or can be seen only with difficulty, from the outside by the operating surgeon. This particular contour line now provides the operating surgeon with an indicator of where on the head the mandrel of greater diameter sits and where the mandrel of smaller diameter sits. The same applies when, for example, three such shaft-like mandrels are provided, and the envelope curve is then designed, for example, as a rounded triangle or as a kind of V-shaped or kidney-shaped body, which is correspondingly rounded. Here too, the operating surgeon always has an indication of where the mandrels extend, even when he barely sees them.

In another embodiment of the invention, at least one mandrel is mounted releasably on the head.

This measure has the considerable advantage that a mandrel that is present can be replaced by another one. This is advantageous, for example, if mandrels of different lengths are to be used. Thus, in laparoscopy, the depth of penetration in a fully grown adult is different than in the case of a child of small frame, for example. However, it is not only possible to use mandrels with different lengths but also, as was mentioned at the outset, with different tip geometries, depending on what is best for the intervention. It is also possible in principle for trocars with different shaft diameters to be exchanged, in which case corresponding measures have to be taken to ensure that these replacement mandrels also fit securely on the head.

In another embodiment of the invention, the at least one releasable mandrel can be connected releasably to the head via a locking mechanism, wherein an actuating element is arranged on the head and permits release of the locking mechanism between the head and the mandrel.

This measure has the advantages that the replacement procedure is easy to carry out and that, by virtue of the locking mechanism, the mandrel fits on the head sufficiently securely and cannot come loose. There are various design options here, for example ball-type locks or the like, as are used in instrument design for releasable connection between a shaft-like body of this kind and a base structure.

In another embodiment of the invention, an adjustment mechanism is arranged on the head and allows the distance between adjacent mandrels to be changed.

This measure has the considerable advantage that the distance between the mandrels mounted on the head can be changed, such that it is possible to adapt in a particularly flexible manner to particular situations.

In combination with the embodiment of the releasable mandrel, a large number of embodiments and structures can now be achieved that are all mounted on one and the same head of the trocar mandrel. These can be mandrels with differently configured tip geometries, different lengths, different diameters, different shaft geometries or the like.

In another embodiment of the invention, on the side of the head from which the shaft-like mandrels protrude, abutments are arranged which limit a depth of insertion of the respective mandrel in a trocar sleeve.

This measure has the advantage that the trocar mandrel can be pushed into the trocar sleeve or, conversely, that the trocar sleeve can be pushed onto the mandrel, only as far as the abutment. This gives the operating surgeon a tactile indication that the assembled device made up of the respective trocar sleeve and of the corresponding mandrel has been obtained with the correct relative position of these two structural parts.

In another embodiment of the invention, an abutment is designed as a stub which projects from the head and in which a proximal area of the mandrel is received.

In the case of mandrels with a relatively large diameter, this measure has the advantage that a relatively bulky mandrel of this type is held particularly firmly and securely by the stub. Since the stub has to be made with a correspondingly larger diameter, the body of the stub can at the same time be designed as such an abutment, for example the distal front edge thereof.

In another embodiment of the invention, openings are recessed in the head, in which openings a proximal end section of a mandrel can be received.

This measure has the considerable advantage that the connection between head and mandrel can be made over a relatively great length and therefore stable.

In embodiments in which the mandrels are connected fixedly to the head, they can be screwed in via threads, adhesively bonded or also welded, for example. In embodiments with exchangeable mandrels, these openings at the same time provide guides, such that the exchangeable shaft, or the distal end thereof, can be guided specifically, for example, to a locking mechanism or releasable coupling.

It will be appreciated that the aforementioned features and the features still to be explained below can be used not only in the cited combinations but also in other combinations or singly, without departing from the scope of the present invention.

BRIEF DESCRIPTION OF THE DRAWINGS

The invention is described and explained below on the basis of a number of selected illustrative embodiments and with reference to the attached drawings, in which:

FIG. 7 shows a side view of a third illustrative embodiment of a trocar mandrel in a similar design to the trocar mandrel from FIG. 1, except that one of the two mandrels is mounted releasably on the head, FIG. 8 shows a view of the trocar body from FIG. 7 partially in longitudinal section, with a mandrel released from the head.

DESCRIPTION OF PREFERRED EMBODIMENTS

Figure 1:
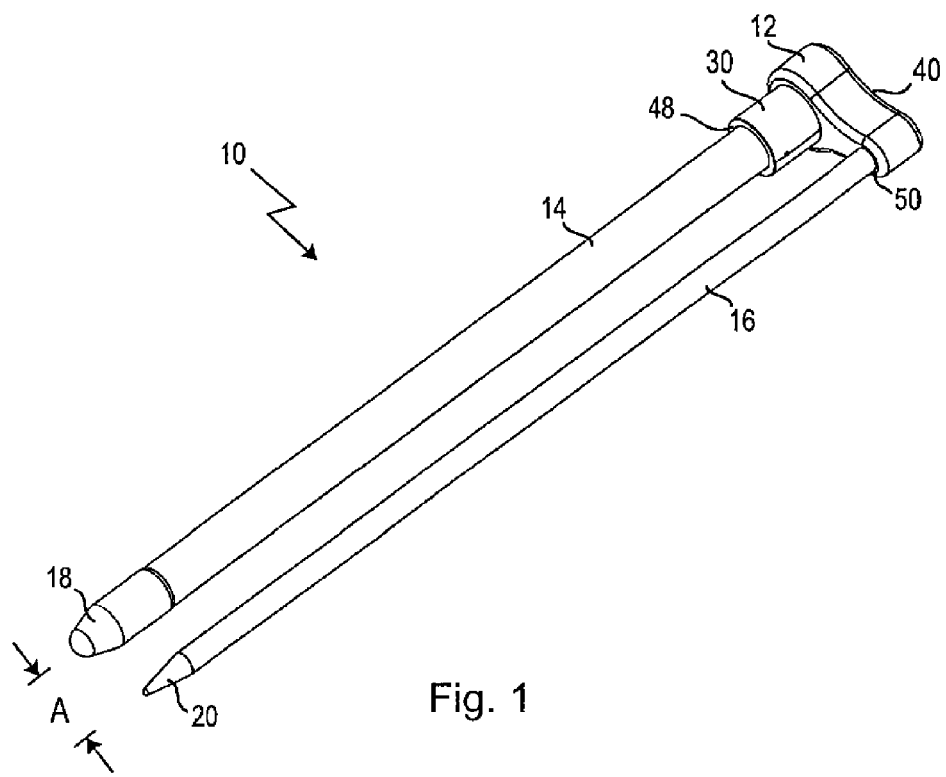
FIG. 1 shows a perspective view of a first illustrative embodiment of a trocar mandrel according to the invention, with two mandrels arranged at a distance from each other and having different diameters.

A first illustrative embodiment of a trocar mandrel is shown in FIGS. 1 to 5, said trocar mandrel being designated overall by reference number 10.

The trocar mandrel 10 has a head 12 from which a first mandrel 14 and a second mandrel 16 extend in the same direction and parallel to each other. Each of the mandrels 14, 16 has a tip 18, 20, respectively, at the distal end. At the proximal end, as can be seen in particular from the sectional view in FIG. 2, the mandrels 14 and 16 are received in openings 22 and 24, respectively, of the head 12. A proximal end section 26 of the first mandrel 14 engages in a first opening 22 in the head 12 and is securely anchored there. The external diameter of the first mandrel 14 corresponds to the clear internal diameter of the opening 22. Securing can be provided by adhesive bonding, welding, or by fixing pins.

A stub 30 extends in the distal direction from the head 12 and surrounds the opening 22.

This stub 30 provides an additional support and guide for the relatively large mandrel 14, which has a diameter 34 of 11 mm, which is larger than the diameter 38 of the second mandrel 16, which is 5.5 mm.

Figure 2:
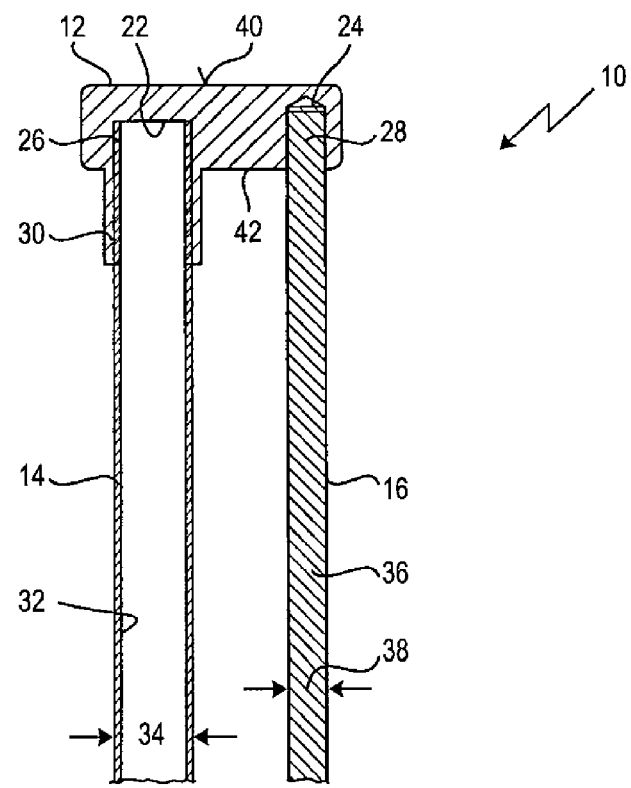
FIG. 2 shows a partial longitudinal section through the trocar mandrel from FIG. 1.

As can be seen from the sectional view in FIG. 2, the first mandrel 14 is designed as a hollow body 32.

The second mandrel 16, with the smaller diameter 38, is designed as a solid rod 36, which is welded into the opening 24.

Figure 5:
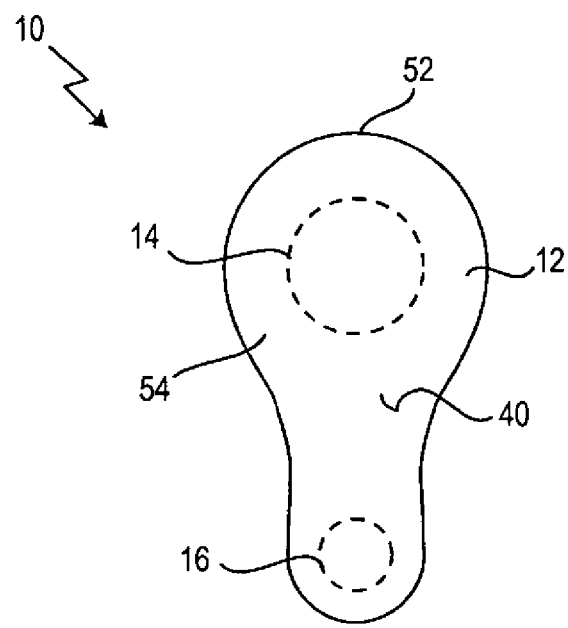
FIG. 5 shows a plan view of the proximal cover face of the trocar mandrel from FIG. 1.

The head 12 has a flat proximal cover surface 40, as can be seen in particular from the views in FIG. 2 and FIG. 5. The proximal cover surface 40 is closed, and the two mandrels 14 and 16 extend from the opposite distal end 42 of the head 12. The two mandrels 14 and 16 are thus arranged at a distance A from each other, as indicated in FIG. 1.

It will be seen from FIG. 5 that a circumferential profile 52 of the proximal cover surface 40 corresponds approximately to an envelope curve surrounding the two mandrels 14 and 16 of different diameter.

This results in a rounded head body 54 that can be gripped particularly ergonomically by hand. The proximal cover surface 40 additionally forms an engagement surface during the handling of the trocar mandrel 10, as will be described below.

Figure 3:
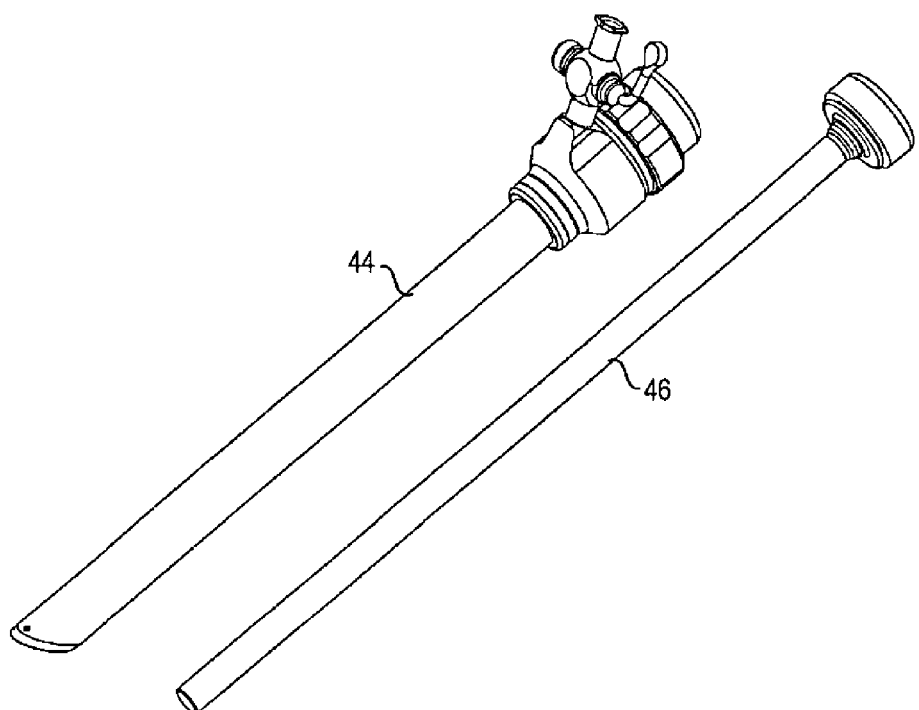
FIG. 3 shows a perspective view of two trocar sleeves that can be pushed onto the two mandrels as are shown in FIG. 1.

FIG. 3 shows a first trocar sleeve 44, of which the sleeve diameter is such that this first trocar sleeve 44 can be pushed with a matching fit onto the first mandrel 14.

Correspondingly, a second trocar sleeve 46 is designed such that it can be pushed with a matching fit onto the second mandrel 16.

The annular distal front face of the stub 30 forms an abutment 48 up to which the first trocar sleeve 44 can be pushed on. The area of the distal end 42 around the second mandrel 16 then forms an abutment 50 for the second trocar sleeve 46.

Figure 4:
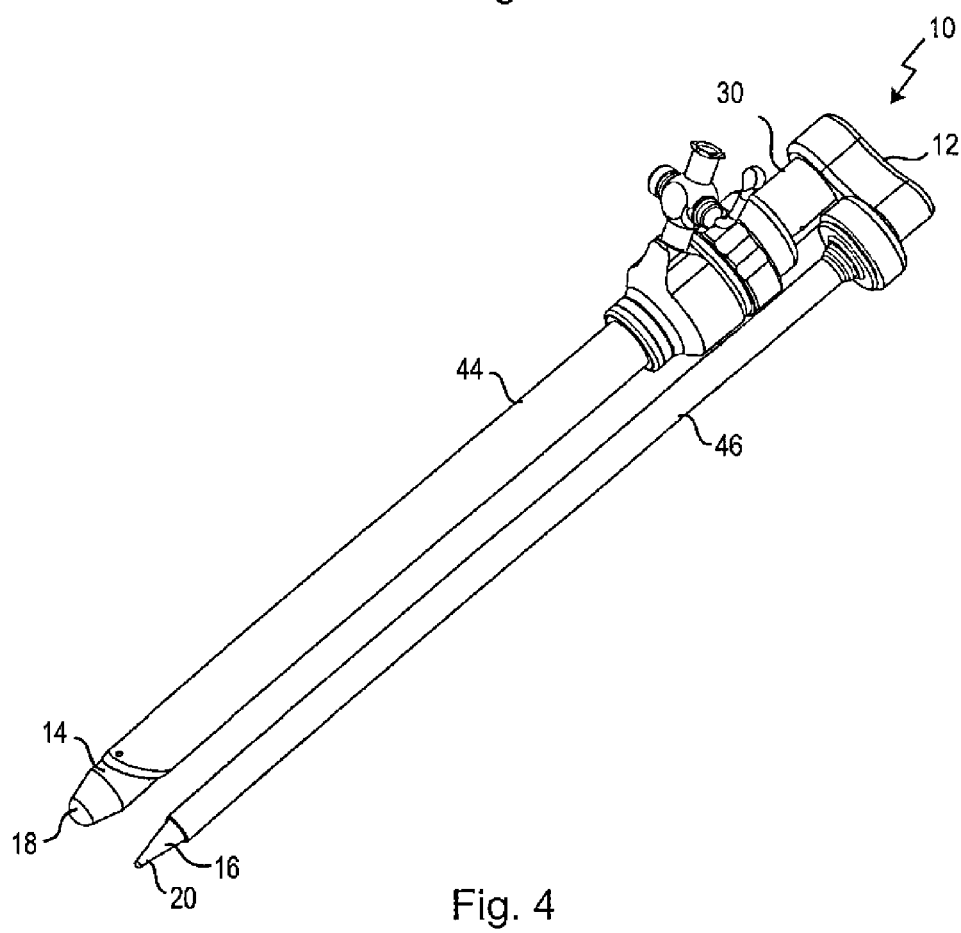
FIG. 4 shows a perspective view of an assembled device made up of the trocar mandrel from FIG. 1 and the two trocar sleeves from FIG. 3 to give the resulting trocar.

FIG. 4 now shows an assembled device in which the first trocar sleeve 44 is pushed onto the first mandrel 14 and the second trocar sleeve 46 is pushed onto the second mandrel 16.

In the assembled state shown in FIG. 4, a trocar has now been formed which, over the two mandrels 14 and 16, has two trocar sleeves 44 and 46 arranged in parallel and at a defined distance from each other.

As can be seen from the view in FIG. 4, the tips 18 and 20 of the mandrels 14 and 16 protrude from the trocar sleeves 44 and 46 at the distal end.

During handling, this assembled device can now be picked up and, for example in a laparoscopic intervention, applied to two incisions on the abdominal wall, with the two tips 18 and 20 being placed on these incisions.

By applying pressure to the proximal cover surface 40 of the head 12, it is now possible to push the trocar through the abdominal wall. After application, the trocar mandrel 10 is withdrawn, and the two trocar sleeves 44 and 46 remain in the abdominal wall, specifically in the desired orientation and especially at the desired distance A from each other. The desired minimally invasive intervention can now be performed through the trocar sleeves 44 and 46.

Figure 6:
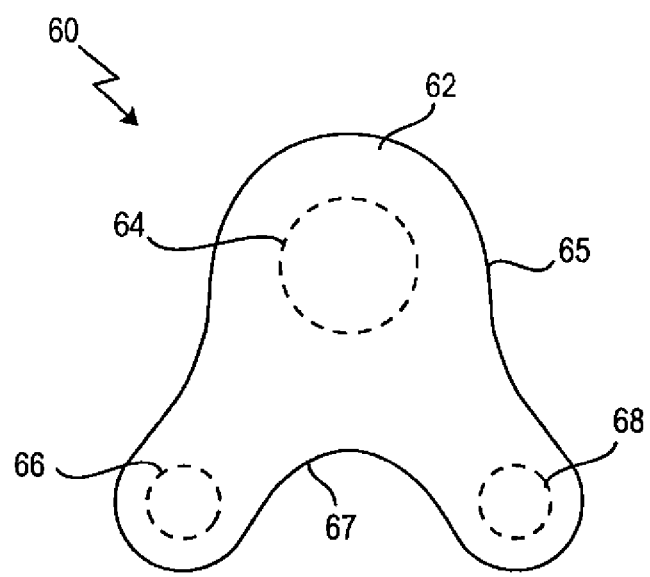
FIG. 6 shows a corresponding plan view of a second illustrative embodiment of a trocar mandrel with three mandrels.

FIG. 6 shows a plan view of a head 62 of a second illustrative embodiment of a trocar mandrel, which is designated overall by reference number 60. It will be seen that the head 62 receives a first mandrel 64, which in size and diameter corresponds approximately to the first mandrel 14 of the first illustrative embodiment.

In the second embodiment, a second mandrel 66 and a third mandrel 68 are present, said two additional mandrels 66 and 68 having a smaller diameter than the first mandrel 64.

The distance of the second mandrel 66 from the first mandrel 64 and the distance of the third mandrel 68 from the first mandrel 64 are approximately the same, said distance also corresponding approximately to the distance between second mandrel 66 and third mandrel 68. The circumferential profile 65 of the head 62 can again be regarded as a kind of envelope line around the three mandrels 64 to 68 and once again results in an ergonomically rounded body 67.

A body 67 of this kind can be safely and ergonomically gripped in one hand, such that a trocar mandrel 60 of this kind, with trocar sleeves pushed onto the three mandrels 64 to 68, can be manoeuvred safely. Thus, three trocar sleeves can then be placed in the body at a very defined distance from each other and in a very defined geometric arrangement to each other, in this case lying at the corners of what is approximately an isosceles triangle.

A third illustrative embodiment of a trocar mandrel, shown in FIGS. 7 and 8, is designated overall by reference number 70.

In terms of its main components, the trocar mandrel 70 is of a similar design to the trocar mandrel 10, i.e. it has a head 72 on which are mounted a first mandrel 74 and a second mandrel 76 of smaller diameter, Thus, the basic design of the head and of the two mandrels 74 and 76 is the same as in the trocar mandrel 10.

In contrast to the first illustrative embodiment, the second mandrel 76 is mounted releasably on the head 72. For this purpose, a locking mechanism 78 is provided in the head 72 and the second mandrel 76.

This locking mechanism 78 has a circumferential groove 80 on the second mandrel 76.

Several spring-loaded balls 82 are arranged in the opening 81 in the head 72, into which opening the distal end section of the second mandrel 76 can be pushed, as is indicated by the arrow 91.

These balls 82 sit in lateral recesses and are pressed in the direction of the interior of the opening 81 by the corresponding springs. The position is such that, when the second mandrel 76 is pushed fully into the opening 81, the balls 82 can engage in the groove 80. An actuating element 84 serves to release this ball locking mechanism 78.

For this purpose, the actuating element 84 can be moved in the direction of the balls 82 counter to the force of a spring 86, as is indicated by the arrow 93. A distal circumferential edge 90 of the actuating element 84 is bevelled, such that a movement of the actuating element 84 in the direction of the arrow 93 counter to the force of the spring 86 presses the ball 82 radially outwards, such that the locking mechanism 78 is then released.

At the upper proximal end, the actuating element 84 is designed as a button 88 that protrudes above the distal cover surface of the head 72, as can be seen in particular from FIG. 7.

To secure the second mandrel 76 in the head 72, it is simply pushed into the opening 81, as can be seen from FIG. 8, until the balls 82 engage in the groove 80.

To release it, the button 88 is pressed in, as a result of which the balls disengage and the second mandrel 76 can be removed.

With the trocar mandrel 70, this opens up the possibility of exchanging the second mandrel 76, for example with a trocar mandrel having a different cross-sectional geometry or having another tip characteristic, another length or the like.

In principle, it is also possible, if so desired, for the first mandrel 74 also to be made releasable.

In this way, the first mandrel 74 could then also be exchanged, such that it would then be possible, depending on requirements, to exchange only one of the two mandrels or else both mandrels 74 and 76.

In the fourth illustrative embodiment of a trocar mandrel according to the invention, shown in FIGS. 9 to 12, the trocar mandrel is designated overall by reference number 100.

The trocar mandrel 100 has a head 102, which is made up of a first part 104 and of a second part 114.

The first part 104 has a distally projecting stub 106, in which a first mandrel 108 is inserted. A flat bracket 110, in which a slit 112 is formed, extends away from the stub 106 approximately at right angles thereto.

Approximately in a mirror image to this, a stub 116, in which a second mandrel 118 is received, likewise extends in the distal direction away from the second part 114.

In this illustrative embodiment, the diameter of the first mandrel 108 and of the second mandrel 118 is equal. A bracket 120, which has a slit 122, also extends away from the second part 114.

Figure 9:
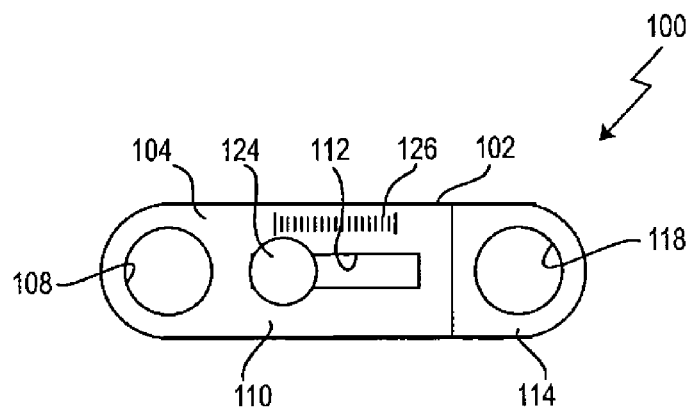
FIG. 9 shows a plan view of the proximal cover surface of the head of a fourth illustrative embodiment of a trocar mandrel, with an adjustment mechanism for changing the distance between two mandrels, in a state with a minimum distance A between the two mandrels.
Figure 11:
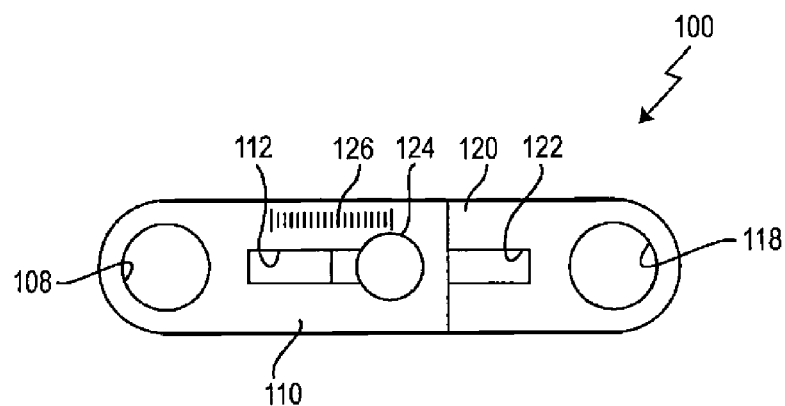
FIG. 11 shows a plan view comparable to the view in FIG. 9, with the distance between the two mandrels having been increased to a maximum distance.

In the assembled state, and as can be seen in particular from FIGS. 9 and 11, the two flat brackets 110 and 120 are laid one over the other, in such a way that the slits 112 and 122 thereof lie one over the other.

A tommy screw 124, which is used to connect these two parts 104, 114 firmly to each other, extends through both slits 112, 122. It will be seen from the plan view in FIG. 9 that a scale 126 is arranged on the top face of the bracket 110.

These structural elements, that is to say brackets 110, 120, slits 112, 122 and tommy screw 124, together constitute an adjustment mechanism 128. The distance A between the two mandrels 108 and 118 can be changed via this adjustment mechanism 128.

Figure 10:
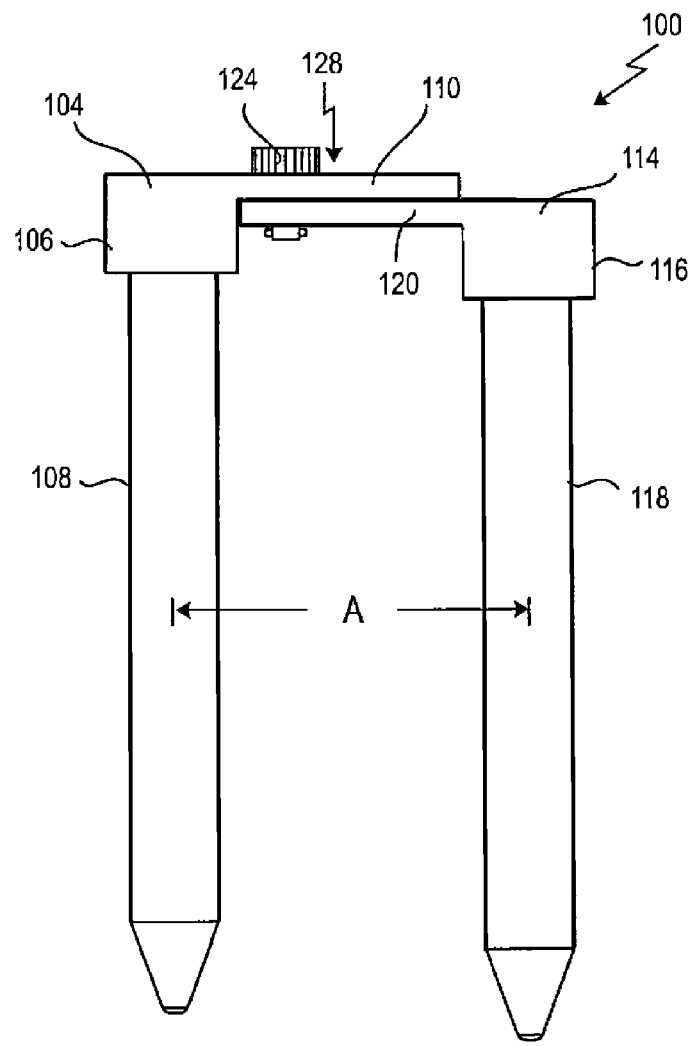
FIG. 10 shows a side view of the trocar mandrel from FIG. 9.

In the view in FIGS. 9 and 10, the distance A is the minimum extent of the distance. That is to say, the two brackets 110 and 120 are moved towards each other to the maximum extent and are fixed on each other via the tommy screw 124.

Figure 12:
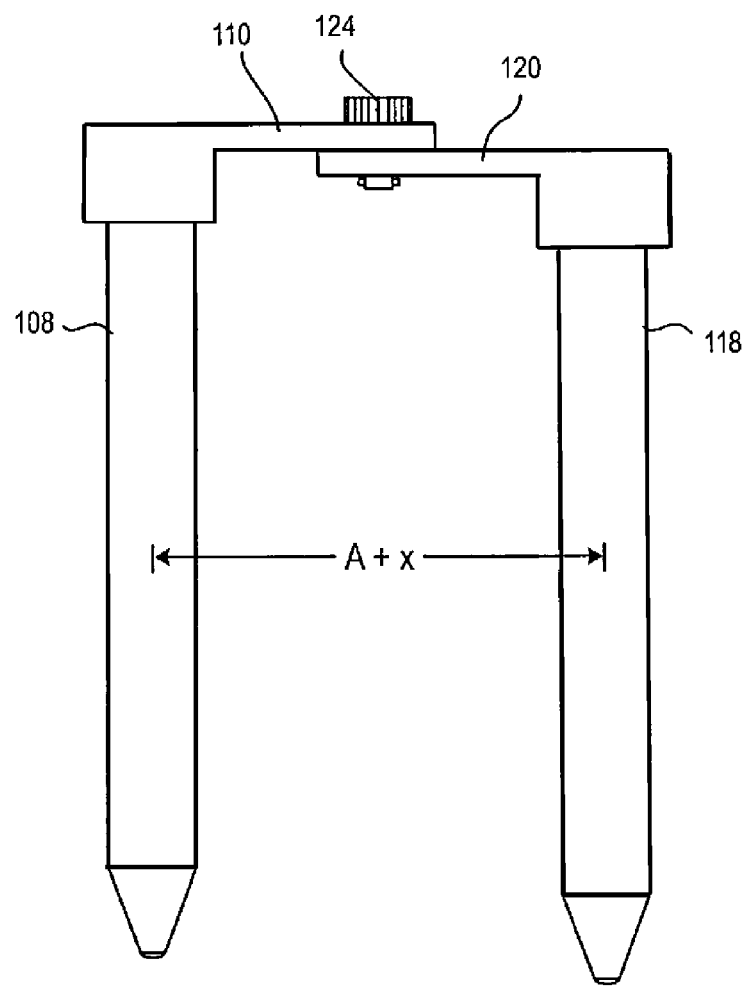
FIG. 12 shows a side view corresponding to FIG. 10, with the trocar mandrel spaced apart to this maximum extent.

By releasing the tommy screw 124, it is possible for the two parts 104 and 114, and the mandrels 108, 118 secured thereon, to be changed in terms of distance by being pulled apart, in which connection FIGS. 11 and 12 now show the maximum distance A+x. It will be seen in particular from FIG. 11 that, in this position, the tommy screw 124 abuts the right-hand end of the slit 112 and, at the same time, the left-hand end of the slit 122 arranged underneath.

Overall, therefore, the distance between the two mandrels 108, 118 can be varied between the distance A shown in FIG. 10 and the distance A+x shown in FIG. 12.

The scale 126 gives the operator a measure for the shift x.

It is also conceivable that, when the tommy screw 124 is released, it is not only possible for the two parts 104, 114 to be moved along the longitudinal extent of the slits 112, 122, but also to be angled away from or towards each other and fixed in the angled state.

Provision can also be made for the variant shown in FIGS. 7 and 8, in which a mandrel is releasable, to be provided also in the fourth illustrative embodiment, such that a particularly high degree of flexibility is achieved as regards the spacing and the configuration of the mandrels to be used.

What is claimed is:

1. A trocar mandrel, comprising
   a head,
   a first mandrel having an elongated shaft, a proximal end of said first mandrel being mounted at said head, said shaft having a closed tip at its distal end,
   at least one second mandrel having an elongated shaft and a closed distal tip, a proximal end of said second mandrel being mounted at said head, said first and second mandrels are mounted at a distance one to another and project from a distal face of said head but do not project from a proximal face of said head,
   said head having a closed flat proximal cover surface extending in a single plane, a circumferential profile of said cover surface corresponds to a contour line completely enveloping said mandrels, and
   said first mandrel and said at least one second mandrel are mounted non-articulating at said head,
   wherein on that side of the head from which said mandrels protrude, abutments are arranged which limit a depth of insertion of a respective mandrel into a trocar sleeve.

2. The trocar mandrel of claim 1, wherein a diameter of said first mandrel differs from a diameter of at least one of said second mandrels.

3. The trocar mandrel of claim 1, wherein said closed flat proximal cover surface of said head serves as a grip.

4. The trocar mandrel of claim 3, wherein said head, seen onto said proximal cover surface, is designed as a rounded body.

5. The trocar mandrel of claim 1, wherein at least one of said mandrels is mounted releasably on said head.

6. The trocar mandrel of claim 1, wherein said abutment is designed as a stub projecting from said head, and wherein a proximal end section of a mandrel is received in said stub.

7. The trocar mandrel of claim 1, wherein openings are recessed in said head, into which openings a proximal end section of a mandrel can be received.

\* \* \* \* \*